United States Patent [19]

Kaetsu et al.

[11] 4,359,483

[45] Nov. 16, 1982

[54] PROCESS FOR PRODUCING A MULTI-LAYERED SLOW RELEASE COMPOSITE

[75] Inventors: Isao Kaetsu; Masaru Yoshida, both of Takasaki, Japan

[73] Assignee: Japan Atomic Energy Research Institute, Tokyo, Japan

[21] Appl. No.: 233,135

[22] Filed: Feb. 10, 1981

[30] Foreign Application Priority Data

Feb. 27, 1980 [JP] Japan ................................ 55/23878

[51] Int. Cl.³ .................... A01N 1/02; B05D 3/00; B05D 3/06
[52] U.S. Cl. .................................. 427/2; 424/19; 424/21; 424/33; 427/3; 427/36; 427/53.1; 427/214; 427/222; 427/398.1; 428/407
[58] Field of Search .............. 427/2, 3, 214, 222, 427/399, 400, 407.1; 428/407, 403; 424/19, 21, 32, 33

[56] References Cited

U.S. PATENT DOCUMENTS

| | | | |
|---|---|---|---|
| 4,252,786 | 2/1981 | Weiss et al. | 424/19 |
| 4,267,138 | 5/1981 | Dobo et al. | 424/19 X |
| 4,282,287 | 8/1981 | Grese | 427/214 X |
| 4,289,795 | 9/1981 | Bogentoft et al. | 424/19 X |

*Primary Examiner*—Michael R. Lusignan
*Attorney, Agent, or Firm*—Browdy and Neimark

[57] ABSTRACT

A process is herein disclosed for producing a multi-layered slow release composite comprising: a first step wherein one or more physiologically active substances is mixed with one member selected from the group consisting of one or more supercooling polymerizable vinyl monomers, one or more natural or synthetic polymeric substances and a mixture thereof, and the mixture is given a predetermined shape and subjected to a physical treatment to form a slow release composite; a second step wherein a predetermined thickness of coating of one member selected from the group consisting of one or more supercooling polymerizable vinyl monomers, one or more natural or synthetic polymeric substances and a mixture thereof is formed on the surface of said slow release composite, which then is subjected to a physical treatment so that a layer wherein no physiologically active substance is encapsulated is formed on the surface of said slow release composite; a third step wherein a predetermined thickness of coating of a mixture of one or more physiologically active substances with one member selected from the group consisting of one or more supercooling polymerizable vinyl monomers, one or more natural or synthetic polymeric substances and a mixture thereof is formed on the surface of the slow release composite having the layer provided in the second step wherein no physiologically active substance is encapsulated, said composite then is subjected to a physical treatment to form a layer wherein the physiologically active substance is encapsulated.

2 Claims, 3 Drawing Figures

PROCESS FOR PRODUCING A MULTI-LAYERED SLOW RELEASE COMPOSITE

SUMMARY OF THE INVENTION

This invention relates to a process for producing a multi-layered slow release composite. More particularly, this invention relates to a multi-layered slow release composite wherein layers having a physiologically active substance encapsulated therein alternate with layers having no physiologically active substance encapsulated therein.

DETAILED DESCRIPTION OF THE INVENTION

Figure 1:
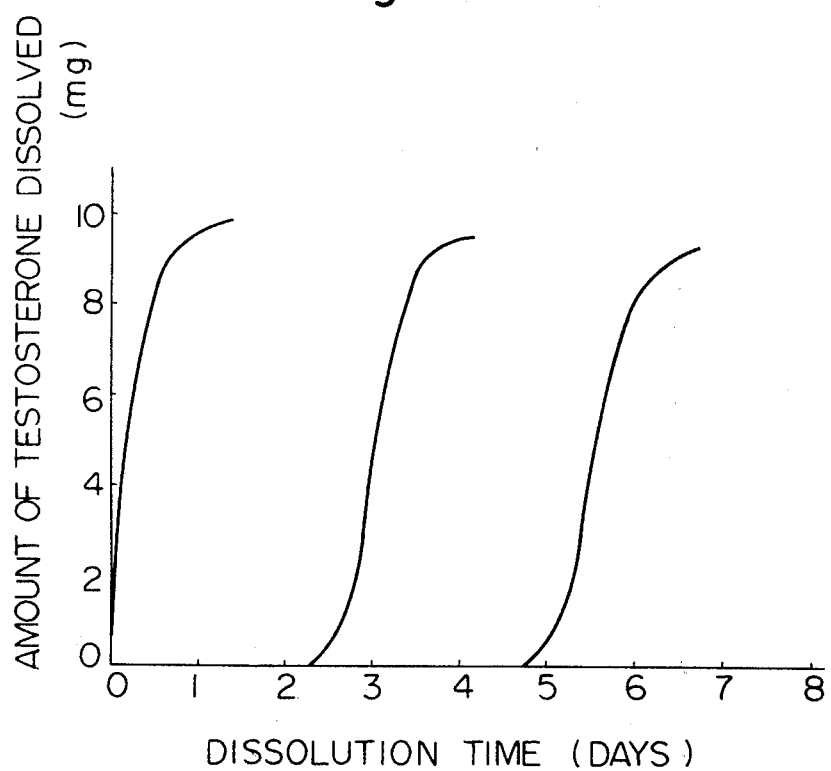
FIGS. 1 to 3 are graphs showing the results of tests conducted to see how various physiologically active substances dissolved out of the slow release composites produced according to the process of this invention.

This invention relates to a process for producing a multi-layered slow release composite. More particularly, this invention relates to a multi-layered slow release composite wherein layers having a physiologically active substance encapsulated therein alternate with layers having no physiologically active substance encapsulated therein.

Several methods have been proposed of making a composite that has a physiologically active substance encapsulated in a polymer or like materials and which slowly releases the physiologically active substance at a controlled rate (such composite is herein referred to as "a slow release composite"). We have also accomplished a basic invention and improved inventions on the same subject. The conventional slow release composite has a physiologically active substance dispersed, fixed and encapsulated in protein or a natural or synthetic polymer matrix and is capable of releasing the physiologically active substance slowly and continuously at a controlled rate, but because of its structure, the composite is not capable of achieving intermittent release of the physiologically active substance, i.e. it is not able to release said substance at intervals. But some physiologically active substances are produced in the living body at intervals, and there are physiologically active substances which, when administered to the living tissue, are desirably released at intervals. This invention is the result of our efforts to meet such demand.

Basically, the process of this invention consists of the following: a first step wherein one or more physiologically active substances (which is hereunder sometimes referred to as "component A") is mixed with one matrix component selected from the group consisting of one or more natural or synthetic polymeric substances (which is hereunder sometimes referred to as "component B"), one or more supercooling polymerizable vinyl monomers (which is hereunder sometimes referred to as "component C") and a mixture thereof, and the resultant mixture is given a predetermined shape and subjected to a suitable physical treatment depending upon the matrix component to modify or polymerize the matrix component so as to form a slow release composite having component A encapsulated in the matrix; a second step wherein a predetermined thickness of coating of component B and/or component C is formed on the surface of a core made of the slow release composite prepared in the first step and the core is subjected to a suitable physical treatment depending upon the component B or C to modify or polymerize the resulting coating so that a layer wherein no physiologically active substance is encapsulated (such layer is hereunder referred to as "an interval layer") is formed on the surface of the core; and a third step wherein a predetermined thickness of coating of a system composed of components A, B and/or C is formed on the surface of the interval layer, and the composite is subjected to a suitable physical treatment depending upon the component B or C to modify or polymerize the component B or C so that a layer having the physiologically active substance encapsulated therein is formed on the surface of the interval layer. By the basic process of this invention described above, a 3-layered slow release composite consisting of the core having the physiologically active substance encapsulated therein, the interval layer having no physiologically active substance encapsulated therein and the outermost layer having the physiologically active substance encapsulated therein is produced. A slow release composite made of four or more layers can be produced by repeating the second and third steps as many times as desired.

The construction of the slow release composite produced by the process of this invention and the physical treatments employed are described hereunder in detail. As mentioned above, the process of this invention uses the component B and/or component C as a matrix component in which the physiologically active substance is dispersed, fixed and encapsulated and as a component of the interval layer. Therefore, the layer for encapsulating the physiologically active substance may be composed of the components A and B, the components A and C or the components A, B and C. The interval layer wherein no physiologically active substance is not encapsulated may be made of the component B or C or both components B and C. Examples of the component B include natural polymers such as gelatin, agar, collagen, peptide, albumin, and synthetic polymers such as polystyrene, vinyl acetate resin, polymethyl methacrylate, polyvinyl pyrrolidone, styrene-methyl methacrylate copolymer, methyl acrylate-methacrylic acid copolymer, 2-methyl-5-vinyl pyridine-methyl acrylate-methacrylate copolymer, methyl acrylate-methacrylic acid-methyl methacrylate copolymer, polyvinyl alcohol, cellulose acetate phthalate, cellulose acetate, dimethylaminoethyl methacrylate-methyl methacrylate copolymer, styrene-maleic acid copolymer, hydroxypropyl cellulose, hydroxypropylmethyl cellulose, hydroxyethylmethyl cellulose, hydroxypropylmethyl cellulose phthalate, and methyl cellulose. If the component B is a natural polymer, it may be modified by any of several physical treatments; heat treatment is the most desirable because it is simple and does not produce contaminating impurities. Modification by heat is generally performed at a temperature between room temperature and 100° C., preferably between 30° and 90° C. Needless to say, the temperature is correlated and can be varied, with the time of heat treatment. If the component B is a synthetic polymer, a coating can be formed on the surface of the core by immersing it in a solution of the copolymer in an organic solvent.

The component C or the supercooling polymerizable vinyl monomer is a monomer that does not crystallize and is supercooled at a temperature lower than 0° C. and higher than the glass transition point and which has a maximum initial polymerization rate for a polymerization temperature range lower than 0° C. at about a temperature 50° C. higher than the glass transition point. Examples of the component C include hydroxyethyl methacrylate, hydroxyethyl acrylate, hydroxypropyl methacrylate, hydroxypropyl acrylate, hydroxybutyl methacrylate, hydroxybutyl acrylate, glycol dimethacrylate, triethyleneglycol dimethacrylate, polyethyleneglycol #200 dimethacrylate, polyethyleneglycol #400 dimethacrylate, polyethyleneglycol #600 dimethacrylate, diethyleneglycol diacrylate, diethyleneglycol dimethacrylate, triethyleneglycol diacrylate, polyethyleneglycol #200 diacrylate, polyethyleneglycol #400 diacrylate, polyethyleneglycol #600 diacrylate, trimethylolpropane trimethacrylate, trimethylolethane trimethacrylate, trimethylolpropane triacrylate, trimethylolethane triacrylate and glycidyl methacrylate.

The physical treatment for polymerizing the component C consists of irradiation with light or ionizing radiation at low temperatures. There is no particular limitation on the type of ionizing radiation, and irradiation having high penetrating power such as gamma rays from cobalt 60 and beta rays from strontium 89 are preferred. The total dose to be given is generally in the range of from $5 \times 10^4$ to $5 \times 10^6$ R preferably about $1 \times 10^6$ R. The irradiation temperature is generally in the range of from $-20°$ to $-130°$ C., preferably from $-70°$ to $-100°$ C. One advantage of polymerizing the component C at a low temperature in the range defined above is that slow release composites of various forms can be produced wherein the physiologically active substance is distributed uniformly throughout without losing its activity during processing. For the reasons stated above, when the matrix or interval layer is made of the component C either alone or in combination with the component B, the component C is polymerized by a physical treatment that consists of irradiation with light or ionizing radiation.

Examples of the component A or the physiologically active substance that can be used in this invention include bleomycin hydrochloride, mitomycin C, carbazyl quinone, rhomstin, thioinosine, citarabin, fluorouracil, 1-(2-tetra-hydrofuryl)-5-fluorouracil, citoteine, chlorambutyl, dibromomannitol, thio-TEPA, cyclophosphamide, acetylurine, noradrenaline, serotonin, callicrein, gastrin, secretin, adrenaline, insulin, glucagon, β-methazone, indometasine, ACTH, growth hormone, gonadotrophin, oxytocin, vasopressin, thyroxine, testicular hormone, vesicular hormone, luteal hormone, adrenal cortical hormone, prostaglandin, antihistaminic, hypotensive agent, vasoconstrictor, capillary stabilizer, stomachic/digestive, intestinal control agent, contraceptive, dermatologic bacteriocide/disinfectant, agent for treating parasitic dermal diseases, antiinflammatory, vitamins, enzyme preparations, vaccines, antiprotozoan agent, interferon inducing substances, anthelmintic, agent for treating fish diseases, agrichemicals, auxin gibberellin, cidocainine, abietic acid, insect hormone, etc.

This invention is now described in greater detail by reference to the following examples which are given here for illustrative purposes only and are by no means intended to limit the scope of the invention. In the examples, tests were conducted to see how various physiologically active substance in the slow release composite dissolved into 1000 ml of a medium. The tests were conducted in accordance with USP XIX at 37° C. with a basket rotating at 100 rpm. Unless otherwise noted, all "parts" and "%" are by weight.

EXAMPLE 1

Production of a 3-layered spherical slow release composite having testosterone encapsulated therein Testosterone was dispersed in hydroxyethyl acrylate containing 10% polymethyl methacrylate, and the resulting mixture was added dropwise to methanol ($-78°$ C. as the temperature of Dry Ice) with a pipette. The mixture in methanol was irradiated with gamma rays from cobalt 60 for one hour at a dose rate of $5 \times 10^5$ R/hr. A spherical composite 5 mm in diameter containing 10 mg of testosterone was formed from the irradiated mixture. The composite was immersed in benzene containing 40% polystyrene until a polystyrene coating was formed on the surface of the composite. The composite was set on the spherical center of a polyethylene vessel which was then charged with 10 mg of testosterone and 0.15 g of hydroxyethyl methacrylate containing 10% poly(methyl methacrylate). The composite was cooled to $-78°$ C. and irradiated with $5 \times 10^5$ R of gamma rays from cobalt 60. The irradiated composite was immersed in benzene containing 40% polystyrene to form a polystyrene coating on the surface of the composite. Finally, a (poly)methyl methacrylate/hydroxyethyl methacrylate coating having testosterone encapsulated therein was formed on the composite. By the procedure described above, a 5-layered slow release composite made of three layers having testosterone encapsulated therein and two interval layers was produced. The composite had a diameter of 8 to 10 mm. A test was conducted to see how testosterone in the composite dissolved into ethanol. The test results are shown in FIG. 1 from which one can see that testosterone dissolved out of the composite at intervals of about one day.

EXAMPLE 2

Production of a composite bar having antitumor agents encapsulated therein

Figure 2:
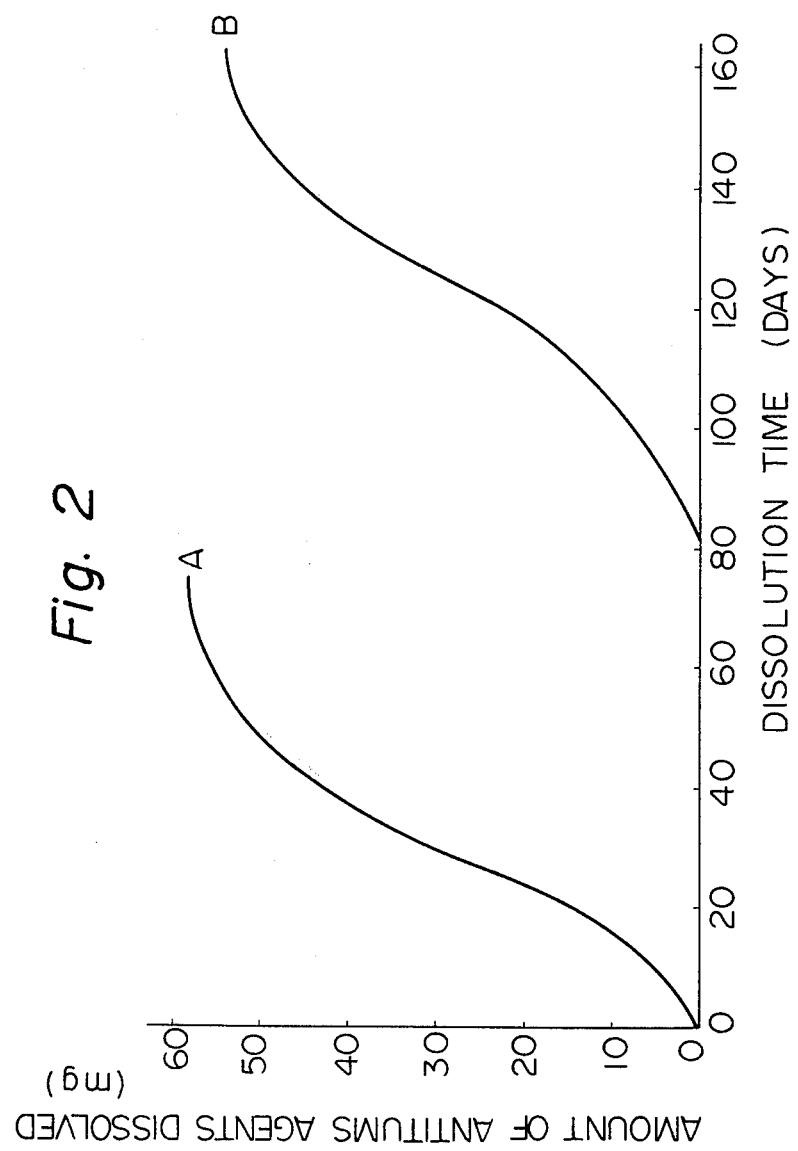

Adriamycin (60 mg) as an antitumor agent was dispersed in 1 g of trimethylolpropane trimethacrylate, and the mixture was irradiated at $-78°$ C. with gamma rays from cobalt 60 at a dose rate of $5 \times 10^5$ R/hr for one hour. A slow release composite bar measuring 0.8 cm in diameter and 1.2 cm in length was shaped from the irradiated mixture. A vinyl acetate polymer coating was formed on the surface of the composite in a thickness of 40 μm. The composite was blended with 1 g of gelatin which had adsorbed 50 mg of mitomycin C, 10 mg of finely divided mitomycin C, and 1 g of diethyleneglycol dimethacrylate containing 10% polystyrene, and the blend was irradiated at $-78°$ C. with gamma rays from cobalt 60 at a rate of $5 \times 10^5$ R/hr to give a total dose of $1 \times 10^6$ R. A slow release composite bar (1.4 cm in dia., 1.8 cm long) made of three layers two of which contained adriamycin and mitomycin C, respectively, was obtained. A test was conducted to see how mitomycin C and adriamycin dissolved into 1000 ml of physiological saline. The test results are shown in FIG. 2 wherein the curve A depicts the dissolution profile of mitomycin C and the curve B depicts the dissolution profile of adriamycin. As is clear from the figure, the interval between the dissolutions of mitomycin C and adriamycin was about 10 days.

EXAMPLE 3

Production of a membranous composite having insulin encapsulated therein

Figure 3:
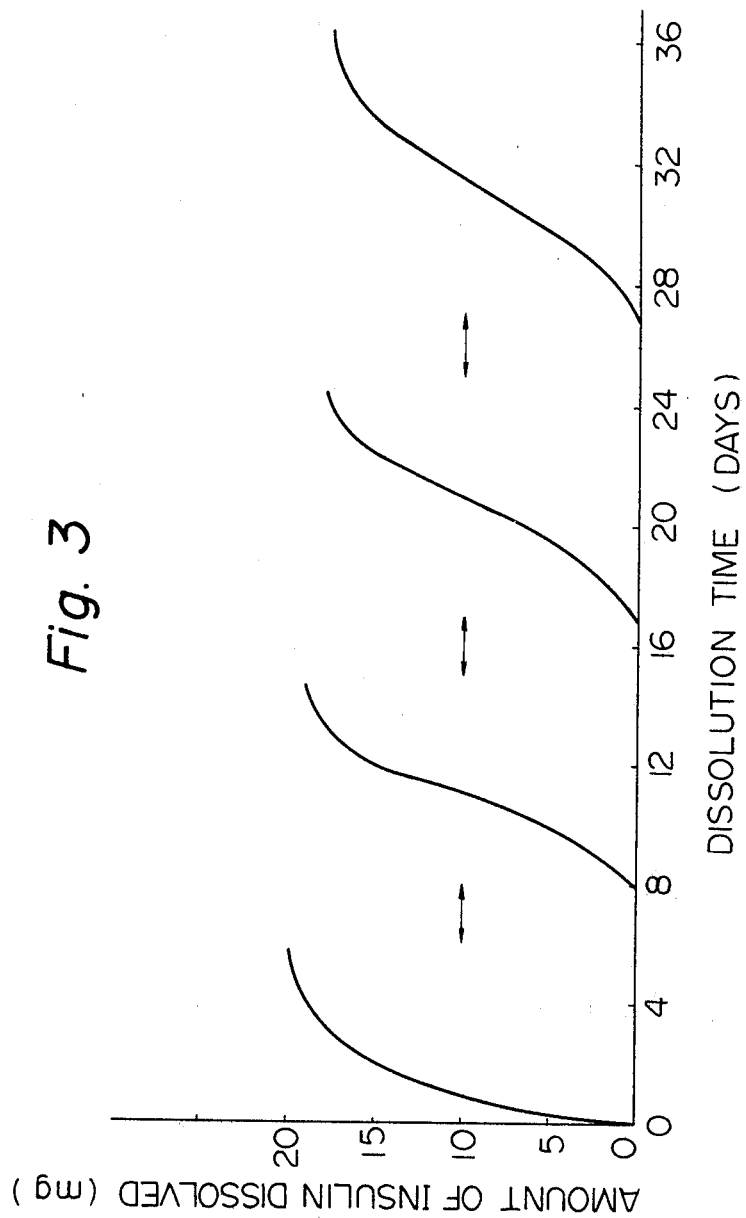

A Mylar film 200 μm thick was placed on both edges of a rectangular glass sheet. A cellulose acetate film 5 μm thick which had the same size as the glass sheet was placed across the Mylar films. A Mylar film 200 μm thick was placed on both edges of the cellulose acetate film. On the cellulose acetate film, two more cellulose acetate films each having a Mylar film on both edges were placed. A rectangular glass sheet was put on the topmost cellulose acetate film. By fixing the top and bottom glass sheets together with a clamper, a hexahedral casing having four space-providing layers each having a thickness of 200 μm and three intervening cellulose acetate films each having a thick of 5 μm was obtained. The resulting four spaces were filled with 20 mg of insulin and 1 g of triethyleneglycol dimethacrylate containing 90% hydroxyethyl acrylate. The casing was cooled to $-78°$ C. and irradiated with gamma rays from cobalt 60 at a rate of $5 \times 10^5$ R/hr to give a total dose of $1 \times 10^6$ R. A slow release membranous composite made of insulin containing layers (200 μm thick) and acetyl cellulose layers (5 μm thick) resulted. A test was conducted to see how insulin dissolved into 1000 ml of 0.2% aqueous hydrochloric acid. The test results are shown in FIG. 3 from which one can see the interval between each dissolution of insulin was about 2 days.

What is claimed is:

1. A process for producing a multilayered slow release composite comprising:
    a first step wherein one or more physiologically active substances is mixed with one member selected from the group consisting of one or more supercooling polymerizable vinyl monomers, and a mixture thereof with one or more natural or synthetic polymeric substances, and the resultant mixture is given a predetermined shape and subjected to irradiation with light or ionizing radiation at $-20°$ to $-130°$ C. to form a slow release composite;
    a second step wherein a predetermined thickness of coating of one member selected from the group consisting of one or more supercooling polymerizable vinyl monomers, one or more natural or synthetic polymeric substances and a mixture thereof is formed on the surface of said slow release composite, which then is subjected to a physical treatment so that a layer wherein no physiologically active substance is encapsulated is formed on the surface of said slow release composite;
    a third step wherein a predetermined thickness of coating of a mixture of one or more physiologically active substances with one member selected from the group consisting of one or more supercooling polymerizable vinyl monomers, and a mixture thereof with one or more natural or synthetic polymeric substances is formed on the surface of the slow release composite having the layer provided in the second step wherein no physiologically active substance is encapsulated, said composite then is subjected to irradiation with light or ionizing radiation at $-20°$ to $-130°$ C. to form a layer wherein the physiologically active substance is encapsulated;
    said second and third steps being optionally repeated as many times as desired so that layers wherein the physiologically active substance is encapsulated alternate with layers wherein no physiologically active substance is encapsulated.

2. A process according to claim 1 wherein the irradiation with light or ionizing radiation is carried out at a temperature between $-70°$ and $-100°$ C.

* * * * *